(12) United States Patent
Appenzeller et al.

(10) Patent No.: US 8,591,512 B2
(45) Date of Patent: Nov. 26, 2013

(54) IMPLANT

(75) Inventors: Andreas Appenzeller, Langendorf (CH); Philippe Gedet, Langendorf (CH); Andre Weber, Solothurn (CH); Christian Gerber, Zumikon (CH)

(73) Assignee: Depuy Synthes Products, LLC, Raynham, MA (US)

( * ) Notice: Subject to any disclaimer, the term of this patent is extended or adjusted under 35 U.S.C. 154(b) by 131 days.

(21) Appl. No.: 13/267,503

(22) Filed: Oct. 6, 2011

(65) Prior Publication Data

US 2012/0116399 A1 May 10, 2012

Related U.S. Application Data (60) Provisional application No. 61/394,107, filed on Oct. 18, 2010.

(51) Int. Cl.
*A61B 17/58* (2006.01)

(52) U.S. Cl.
USPC .......................................................... 606/63

(58) Field of Classification Search
USPC ............ 606/62–64, 278, 279, 263, 281, 246, 606/267, 265, 249, 247, 248; 623/17.11–17.16
See application file for complete search history.

(56) References Cited

U.S. PATENT DOCUMENTS

| | | | | |
|---|---|---|---|---|
| 5,192,326 | A | * | 3/1993 | Bao et al. .................... 623/17.12 |
| 8,252,031 | B2 | * | 8/2012 | Carls et al. .................... 606/279 |
| 8,348,978 | B2 | * | 1/2013 | Trieu et al. .................... 606/278 |
| 2007/0282448 | A1 | * | 12/2007 | Abdou ........................ 623/17.15 |
| 2009/0234457 | A1 | * | 9/2009 | Lotz et al. .................. 623/17.16 |
| 2011/0319996 | A1 | * | 12/2011 | Barrall ....................... 623/17.12 |

FOREIGN PATENT DOCUMENTS

| | | |
|---|---|---|
| WO | 2007/127734 | 11/2007 |
| WO | 2007/140382 | 12/2007 |
| WO | 2010/074704 | 7/2010 |

* cited by examiner

*Primary Examiner* — Pedro Philogene (74) *Attorney, Agent, or Firm* — Fay Kaplun & Marcin, LLP (57) ABSTRACT

An implant comprises a deformable gas tight sack. The sack comprises a first chamber in fluid communication with an obturatable opening, the chamber filled or fillable with a filling material filling the first chamber. The implant is configured such that when one or both of a gas and fluid surrounding the filling material is removed from the first chamber through the opening, a wall of the first chamber forms around and holds the filling material. This causes the implant to transition from a relatively flexible insertion state to a relatively rigid fixation state in which the implant is fixable in the target portions of bone.

20 Claims, 4 Drawing Sheets

IMPLANT

PRIORITY INFORMATION

The present application claims priority to U.S. Provisional Application Ser. No. 61/394,107 entitled "Implant" filed on Oct. 18, 2010 to Andreas Appenzeller, Philippe Gedet, Andre Weber and Christian Gerber. The entire contents of this application are incorporated herein by reference.

FIELD OF THE INVENTION

The present invention generally relates to an implant. More particularly, the present invention relates to a flexible implant that can be evacuated and stiffened in-situ. Embodiments of the invention relate to a method for bone fixation and to the use of the implant for supporting and/or filling a cavity of a bone, such as a medullary canal of a bone or long bone.

BACKGROUND

Bone fractures are often treated with fixation devices such as bone plates, intramedullary nails or other bone fixation elements. Fixation using these devices, however, often requires an invasive surgical procedure.

SUMMARY OF THE INVENTION

The present invention relates to an implant that can be evacuated and can offer the highest possible security against a failure of the implant due to loss of the vacuum.

The present invention further relates to an evacuatable implant which comprises a deformable, gas tight sack, which is filled with a filling material and evacuated of a gas or fluid surrounding the filling material via an obturatable opening to stiffen the implant. Further, the sack comprises a single chamber or a plurality of interconnected chambers which are evacuatable via the opening. The chambers may be filled with the filling material either during or after the manufacturing of the sack.

In one exemplary embodiment of the implant the sack comprises a stiff material. The sack may comprise any suitable polymer, such as PET or PLLA.

In another exemplary embodiment, the sack may be reinforced. The reinforcement may be provided by reinforcement beams, such as metal wires. The beams may run along the length of the sack or may be helically wound around the sack. Alternatively or in addition, the sack may be reinforced with fibers. The fibers may be arranged in mesh or grid that is incorporated into the sack material to reinforce this material during the evacuation process. The fibers may serve to protect the sack material in a way that minimizes damage, such as fissures or tears, that may occur as a result of external influences or during insertion of the implant or should the filling material have sharp edges.

In yet another exemplary embodiment of the implant the opening includes a valve, preferably a stop valve.

In a further exemplary embodiment of the implant the opening may be welded such that the opening is gas tight. In a further alternative embodiment, the opening is configured as a tube like collar that may be tied off.

In again a further exemplary embodiment of the implant the chambers are interconnected by valves, preferably directional control valves or non-return valves. Thereby, the directional control valves allow a flow in either direction when opened and completely obturate the adjoining chambers when closed. The non-return valves allow a flow in one direction only and obturate the adjoining chambers when no flow in the direction occurs and prevent all flow in the opposite direction. Alternatively, the interconnection(s) between the chambers are obturatable by welding or tying off.

Some advantages achieved by this configuration are that security against failure of the implant through damage of the sack is improved. If one of the individual chambers is damaged or begins to leak after evacuation of the implant, the remaining chamber or chambers remain gas tight so that the implant as a whole maintains sufficient stiffness.

In yet a further exemplary embodiment of the implant, the sack comprises a second valve, preferably a second stop valve, via which the sack is fillable with filling material. The second valve is preferably arranged on the side of the sack opposite to the first valve, so that the non-return valves open when filling material is introduced into the chambers via the second valve. If the chambers are interconnected by stop valves or directional control valves the second valve is not necessary because the directional control valves can be opened or closed by a control member so that through flow in both directions is possible.

In still a further exemplary embodiment of the implant the individual chambers are placed in series so that a longitudinal implant is configured.

In another exemplary embodiment of the implant comprises a plurality of chains extending parallel to one another, each of the chains including a plurality of chambers In again another exemplary embodiment of the implant the sack comprises an envelope and dividing walls arranged between the chambers. This configuration of the implant fixes the individual chambers relative to one another when the evacuation of the sack is completed since a vacuum pressure within the chambers stiffens the dividing walls.

In yet another exemplary embodiment of the implant the sack comprises an envelope configured as a flexible tubular connection element between adjacent pairs of chambers and wherein the flexible tubular connection elements are not filled with filling material. With this configuration, individual chambers remain moveable relative to one another after evacuation has been completed so that the chain-like implant may be introduced into a bone cavity such as, for example, an intervertebral space such as a cavity in a vertebral body, filling and augmenting the space.

In a further exemplary embodiment of the implant the individual chambers are arranged relative to one another in parallel as well as in series along a length of the implant. Thus, the implant may be configured as, for example, an intramedullary nail into which locking screws may be inserted via a passage extending through some of the chambers without disturbing a vacuum in the other chambers so that the implant as a whole maintains a desired stiffness.

In again a further exemplary embodiment of the implant the filling material comprises individual particles.

In yet a further embodiment of the implant the individual particles are not round, preferably including edged surfaces. The particles could have a well-defined or regular shape or they could have random shapes. Where the particles have a well defined or regular shape, each of the particles could have the same shape and/or size. This configuration enhances mutual blocking of the individual particles under the effect of the vacuum to prevent the filling material from also being removed during evacuation.

In another exemplary embodiment of the implant the individual particles are formed of a sinterable thermoplastic.

In another exemplary embodiment of the implant the obturatable opening comprises a filter for preventing removal of the filling material during evacuation.

In another exemplary embodiment of the implant the individual particles have a mean diameter less than or equal to 700 microns.

In again another exemplary embodiment of the implant the individual particles have a mean diameter larger than 700 microns.

In yet another exemplary embodiment of the implant the individual particles comprise a dye, a pigment or a chromophore.

In a further exemplary embodiment of the implant the filling material comprises one or more threads or fibers. The one or more threads or fibers can be introduced into the chambers by means of a syringe filled with water.

In again a further exemplary embodiment of the implant the sack comprises an envelope including a plurality of protrusions extending from an outer surface thereof for contacting a bone or tissue surface, to strengthen anchoring of the implant in the surrounding bone material.

In yet a further exemplary embodiment of the implant the sack is evacuated of a gas or fluid surrounding the filling material.

In another exemplary embodiment of the implant the sack comprises a resorbable material.

In again another exemplary embodiment of the implant the filling material comprises a resorbable material. Thus, in cases where the sack is damaged or the sack is resorbed, an outflow of the resorbable particles is not dangerous to the patient.

In yet another exemplary embodiment of the implant two or more chambers are concentric with the innermost chamber containing the filling material.

In still another exemplary embodiment of the implant the sack comprises an envelope and one or more passages extending transversely through the sack. The chambers are gas-tight with respect to the passages. Each passage comprises a first and a second opening in the envelope of the sack so that the passages are suitable for insertion of a fixation element such as a locking screw therein. The sack can have one or more through holes suitable for insertion of a fixation element therethrough without damaging the chambers.

In again another exemplary embodiment of the implant the passages are configured as tubes connected to the envelope at the first and second openings. The tubes may be flexible.

In a further exemplary embodiment the implant further comprises one or more locking screws that can be led through the implant.

In a further exemplary embodiment, the implant has a predetermined insertion shape. Preferably, an outer wall of the sack defines a predetermined insertion shape. Suitably, the outer wall is the wall of the first chamber and/or the plurality of chambers. The predetermined insertion shape may correspond to the size and geometry of a target bone cavity in which the implant is to be inserted. This shape may make it easier for a user of the implant to insert the implant into the target bone cavity. For example, the implant or outer sack wall may have a long cylindrical shape to aid insertion into an intramedullary canal of a bone, such as a long bone.

The present invention also relates to an implant that may be used to support and/or fill a medullary space of a long bone.

The present invention further relates to a method for bone fixation is provided which comprises the steps of inserting the implant, which includes a filling material within chambers thereof, into the medullary space of a long bone, and evacuating the chambers of a gas or fluid surrounding the filling material such that after the chambers have been evacuated, the implant is made rigid.

In an exemplary embodiment the method further comprises the step of obturating the opening after evacuation of the chambers and, when the opening is configured as a valve such as a stop valve, closing the valve. Alternatively, the opening can be obturated by means of welding or tying off. If the opening is configured as a non-return valve, it will be understood by those of skill in the art that the opening obturates automatically.

In a further exemplary embodiment the method comprises the additional step of obturating the interconnection(s) between the chambers and, when the interconnection(s) between the chambers are configured as directional control valve(s) or stop valve(s), closing the valve(s). Alternatively, the interconnection(s) can be obturated by means of welding or tying off.

In another embodiment the method comprises the additional step of sintering the filling material by supplying energy thereto, to prevent the filling material from also being removed during evacuation of the chambers.

BRIEF DESCRIPTION OF THE DRAWINGS

Several embodiments of the invention will be described in the following by way of example and with reference to the accompanying drawings in which.

DETAILED DESCRIPTION

The present invention may be further understood with reference to the following description and the appended drawings, wherein like elements are referred to with the same reference numerals. The present invention relates to the treatment of fractures and, in particular, relates to a minimally invasive device insertable into a bone for fixing a fracture. Exemplary embodiments of the present invention describe a deformable implant including a chamber that may be filled with a filling material and that may be later evacuated of a gas or fluid surrounding the filling material so that the implant is stiffened to fix fractured portions of the bone in desired spatial relations relative to one another. The implant may be filled and/or evacuated via a valve. The valve of the exemplary embodiments may be, for example, a directional control valve.

The directional control valve is a controllable valve comprising at least one passage for a gas, particularly for air. In embodiments where the chambers are filled with the filling material subsequent to manufacturing the sack, the directional control valve may have one or more passages for a flow of the gas and/or of the filling material. For example, the directional control valve may have a first passage for the flow of gas and a second passage for the passage of the filling material. The directional control valve may include a control member having two or three fixed positions. A directional control valve having one passage may include a control member with two fixed positions for opening or closing the single passage. Where the directional control valve includes two passages, the control valve may have three fixed positions for selectively opening either passage and for closing both passages.

Figure 1:
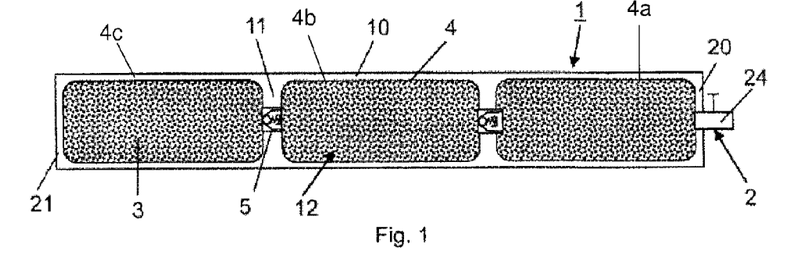
FIG. 1 illustrates a schematic lateral view of an embodiment of the implant according to the invention.

As shown in FIG. 1, an implant according to a first exemplary embodiment includes a gas tight deformable sack 1 extending longitudinally from a first end 20 to a second end 21 and including therein a plurality of chambers 4 in series along a length thereof. The sack 1 may include an opening 2 at the first end 20 of the sack 1 through which a filling material 12 may be supplied to the chambers 4 and/or a gas, such as air, or fluid surrounding the filling material 12 within the chambers 4 is evacuated therefrom. The opening 2 may be configured as a stop valve 24 fixed to the sack 1 and which may be closed when the evacuation of the chambers 4 has been completed. The chambers 4 formed in the sack 1 may be filled with a filling material 12 including individual particles 3. The individual particles 3 may be formed of, for example, a sinterable thermoplastic. In an alternative embodiment, the individual particles may be formed of a dye, a pigment and a chromophore. In another embodiment, the filling material 12 may include threads and/or fibers rather than individual particles 3. The chambers 4 may be filled with the filling material 12 during manufacturing of the sack 1.

The chambers 4 of the sack 1 may be defined by an envelope 10 and dividing walls 11 arranged between adjacent chambers 4, which may be formed of the same flexible material as the envelope 10. Materials such as PET and PLLA can be used to make the envelope 10, but any suitable material can be used as would be understood by the skilled person. In one exemplary embodiment, each pair of adjacent chambers 4 may be connected to one another via a non-return valve 5. Further, the chamber 4 closest to the first end 2 of the sack 1 may be in fluid connection with the opening 2. Thus, applying a vacuum at the opening 2 initially evacuates the first chamber 4a in fluid connection with the opening 2. The non-return valves 5 may be arranged within the dividing walls 11 such that each of the non-return valves 5 directs its flow in the same direction. In addition, the non-return valves 5 open when a pressure in the adjacent chamber 4 is lower. For example, as the vacuum source evacuates the first chamber 4a, the pressure in the first chamber 4a becomes lower than that of an adjacent second chamber 4b, causing gas and/or fluid from the second chamber 4b to flow into the first chamber 4a and through the opening 2. Similarly, as a pressure in the second chamber 4b falls, gas and/or fluid from a third chamber 4c flows into the second chamber 4b. Due to this configuration of the non-return valves 5, all of the chambers 4 may be evacuated via the opening 2. When the evacuation of the sack 1 has been completed, the vacuum within the chambers 4 causes a wall of the chamber to deform and press against the filling material to hold the filling material, for example, under compression. As shown by FIG. 1, the wall of the chamber is the outer wall of the sack 1. The evacuation of the chamber causes the implant to stiffen so that the position of each of the chambers 4 is fixed relative to the others. It will be understood by those of skill in the art that although the deformable sack 1 is shown as including three chambers 4, the deformable sack 1 may include any number of chambers 4.

An exemplary surgical technique according to the present invention, involves inserting the deformable sack 1 including a filling material 12 in the chambers 4 thereof into a medullary canal of a bone. Upon insertion, the implant has a degree of flexibility allowing it to be bent and shaped as it being positioned in the bone. The degree of flexibility is due to the elements of the filling material being able to move relative to each other in the chamber. Once the deformable sack 1 has been inserted to a desired position within the bone, a vacuum force is applied to the opening 2 to remove gas and/or fluid surrounding the filling material 12 from the chambers 4, as described above, until the sack 1 is substantially completely evacuated of gas and/or fluid. The evacuation cause a stiffening of the implant as a wall of the chambers 4 deforms around the filling material. The chambers 4 are evacuated until the implant achieves a desired level of rigidity for fixing the fractured portions of the bone relative to one another. The rigidity is achieved by the wall of the chamber holding the filling material and preventing movement of elements of the filling material relative to each other. As a result, the implant is substantially resistant to, for example, the bending or compression forces it will experience after being fixed in a patient's body.

Figure 2:
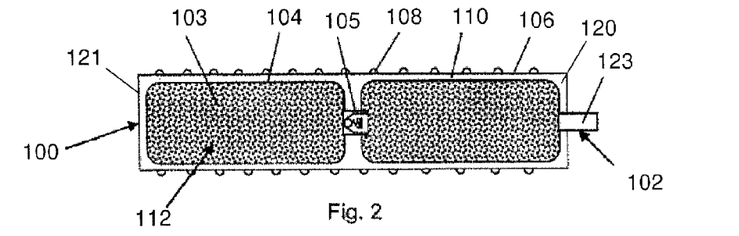
FIG. 2 illustrates a schematic lateral view of another embodiment of the implant according to the invention.

A deformable sack 100 as shown in FIG. 2, is substantially similar to the deformable sack 1 described above, extending from a first end 120 to a second end 121 and including a plurality of chambers 104 arranged along a length thereof with adjacent chambers 104 connected to one another via a non-return valve 105. The sack 100, however, comprises an envelope 110 defining the chambers 104 and having an outer peripheral surface 106 including knobs 108 protruding therefrom. The knobs 108 form point-like rests suitable for contacting a surface of a bone to enhance a grip of the sack 100 on a wall of a medullary canal of a bone into which it has been inserted. The sack 100 further comprises a tubular collar 123 at an opening 102 at a first end 120 of the sack 100. The tubular collar 123 may be welded, e.g. jig welded or tied off, once the chambers 104 of the sack 1 have been evacuated. Analogously to the embodiment of FIG. 1, the chambers 104 may be filled with a filling material 112 including individual particles 103. Similarly, the chambers 104 may be filled with the filling material 112 during manufacturing of the sack 100. Once the sack has been inserted into the medullary canal as desired, the gas and/or fluid surrounding the filling material 112 is evacuated therefrom until the implant stiffens to a desired level of rigidity to fix the fractured portions of the bone in desired positions relative to one another.

Figure 3:
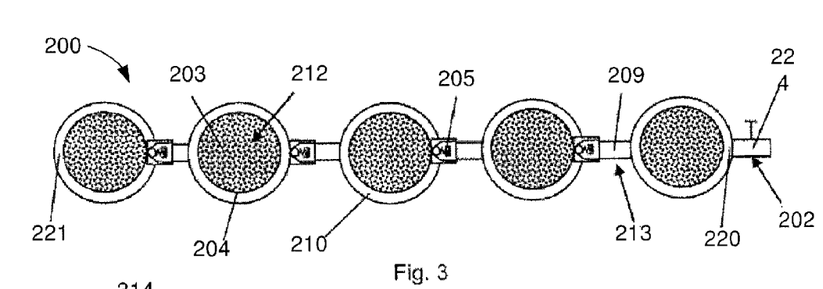
FIG. 3 illustrates a schematic lateral view of again another embodiment of the implant according to the invention.

An elastic sack 200 as shown in FIG. 3 includes a plurality of chambers 204 arranged longitudinally in series. The sack 200 may be substantially similar to the sack 1 extending from a first end 220 to a second end 221 and including an opening 202 arranged at the first end 220 thereof for withdrawing a gas and/or fluid surrounding a filling material 212 in the chambers 204. The opening 202 may be configured as a stop valve 224 fixed to the sack 200 and may be closed when evacuation of the chambers 204 has been completed. Similarly to the sack 1, the chambers 204 may be filled with a filling material 212 including individual particles 203. The chambers 204 may be defined by a flexible envelope 210 including tubular connection elements 213 between adjacent chambers 204. Each of the connection elements 213 may be a flexible tube portion 209 in which a non-return valve 205 is arranged so that adjacent chambers 204 may be separated from each other. Alternatively, the chambers 204 may be separated by a jig welding or tying off of the flexible tube portions 209 so that non-return valves 205 do not have to be arranged in the flexible portions 209. Due to the flexible tube portions 209, the chambers 204 are moveable relative to one another even after completion of the evacuation of the sack 200, so that a chain like implant is formed. A chain-like embodiment of the deformable sack 200 may be used in surgical procedures in which a movable structure is desirable, e.g. for filling a cavity in a bone or an intervertebral space. Where the sack 200 does include non-return valves 205, however, the non-return valves 205 are arranged so that flow is directed through each of the non-return valve 205 in the same direction so that each non-return valve 205 opens when the pressure in an adjacent chamber 4 closer to the opening 202 is lower than the pressure in that chamber 4. Thus, as described in regard to sack 1, the chambers 204 can be evacuated via the opening 202. Similarly to the sack 1, the chambers 204 may be filled with the filling material 212 during manufacturing of the sack 200. When evacuated of the gas and/or fluid surrounding the filling material 212 within the chambers 204, the sack 200 deforms about the filling material 212 causing the implant to stiffen to a desired rigidity to fix the fractured portions of the bone in position relative to one another.

Figure 4:
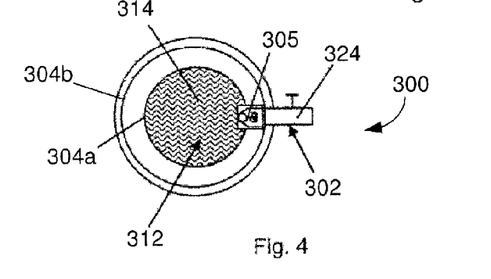
FIG. 4 illustrates a schematic top view of yet another embodiment of the implant according to the invention.

FIG. 4 illustrates an embodiment comprising a spherical or cylindrical implant formed of a gas tight sack 300 comprising two concentrically or coaxially arranged chambers 304a, 304b. The sack 300 may be substantially similar to the sack 1, as described above, including an opening 302 in fluid communication an outer chamber 304b for evacuating a gas and/or fluid surrounding filling material 312 contained in the sack 300. The inner chamber 304a may be filled with a filling material 312 including a plurality of threads 314 or fibers. The threads 314 or fibers may be introduced into the inner chamber 304a using a syringe filled with water so that the threads 314 or fibers can be entrained by the water injected into the chamber 304a. The inner and outer chambers 304a, 34b may be connected to one another via a non-return valve 305 such that the water can be subsequently removed from the inner chamber 304a via the non-return valve 305 and a stop valve 324 arranged at the opening 302. The water may be permitted to flow out of and/or be suctioned out of the opening 302. The non-return valve 305 and the valve 324 at the opening 2 may include a sieve or other suitable filtering element to prevent the filling material 312 from flowing therepast during the evacuation. As similarly described in regard to the sack 1, both chambers 304a, 304b may be evacuated via the stop valve 324, which is fixed to the sack 300 and which may be closed when the evacuation of the chambers 304a, 304b has been complete. The non-return valve 305 is arranged so that it opens when the pressure in the outer chamber 304b, located between the inner chamber 304a and the opening 302 is lower than the pressure in the inner chamber 305. Due to this configuration both chambers 304a, 304b can be evacuated via the opening 302. When the evacuation has been completed the outer walls of the inner and outer chamber 304a, 304b are stiffened so that a rigid implant results.

Figure 5:
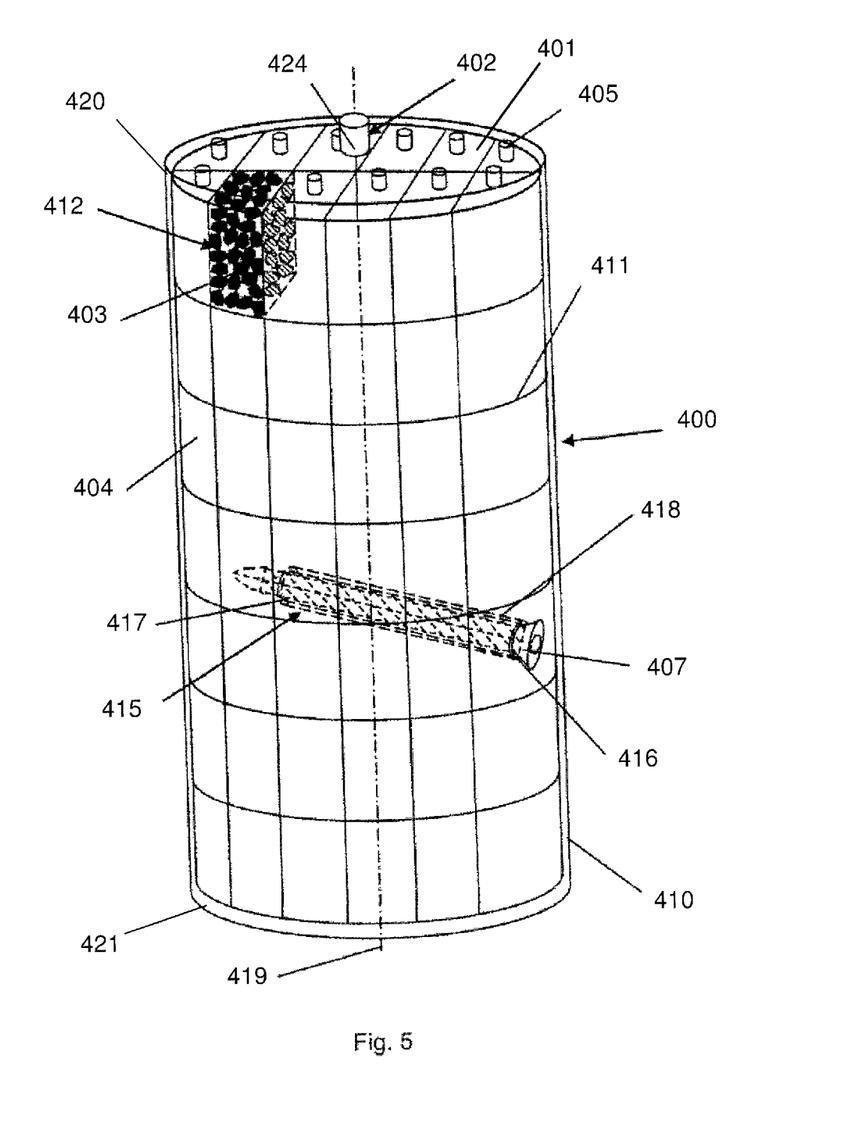
FIG. 5 illustrates a schematic perspective view of still another embodiment of the implant according to the invention.

A sack 400 according to a further embodiment of the invention shown in FIG. 5 comprises a plurality of chains 401, each of which extends parallel to a longitudinal axis 419 of the sack 400. Each of the chains 401 includes a plurality of chambers 404 arranged in series along a length thereof from a first end 420 to a second end 421 of the sack 400. The sack 400 may be substantially similar to the sack 1, described above, including an envelope 410 defining the chambers 404 via dividing walls 411 extending between adjacent chambers 404. The chambers 404 may be filled with a filling material 412 such as, for example, individual particles 403, during manufacturing of the sack 400. Fluid and/or gas surrounding the filling material 412 within the chambers 404 may be evacuated via an opening 402 at the first end 420 of the sack 400. Analogously to the embodiment of FIG. 1, the opening 402 may be configured as a stop valve 424 fixed to the sack 400 and which may be closed when the evacuation of the chambers 404 has been complete. Each pair of adjacent chambers 404 in series in each of the chains 401 may be interconnected by a non-return valve 405. These non-return valves 405 may be integrated in the dividing walls 411 of the sack 400 such that a flow through each of the non-return valves 405 is in the same direction. Thus, non-return each valve 405 opens when a pressure in a chamber 404 open to a side of the valve 405 closer to the opening 402 is lower than the pressure in the adjacent chamber 404 opening into the side of the valve 405 further from the opening 402. Each of the non-return valves 405 at the first end 420 may be in fluid connection with the opening 402 such that the opening 402 permits the evacuation of all of the chambers 404 via the opening 402. The sack 400 may further comprise a passage 415 extending the transversely through the sack 400 such that the passage 415 extends through a number of chambers 404. The number of chambers 404 is gas-tightly sealed with respect to the passage 415 which has first and second openings 416, 417, respectively, in the envelope 410, so that a locking screw 407 may be inserted through the passage 415 from the first opening 416 past the second opening 417. The passage 415 may be configured as a tube or flexible tube 418 fixed to the envelope 410 at the first and second openings 416, 417. Upon evacuation of the chambers 404, the envelope 410 stiffens to provide rigid fixation of the bone. The sack 400 may be used in substantially the same manner as described above in regard to sack 1, but may additionally accommodate the locking screw 407 in the passage 415 to provide further fixation of the sack 400 relative to the bone.

Figure 6:
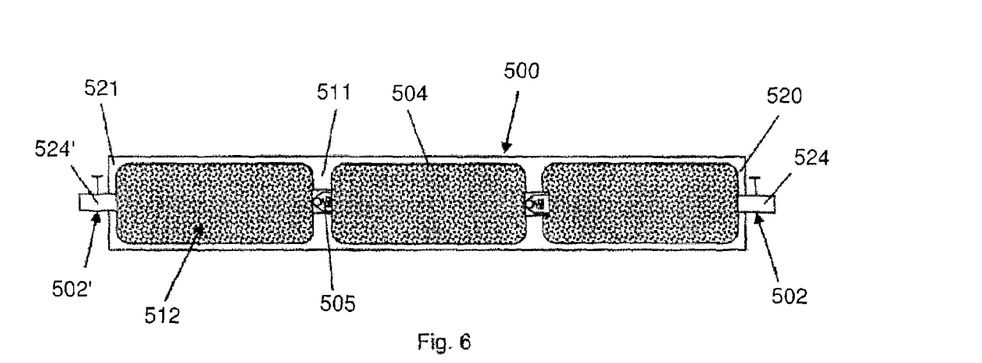
FIG. 6 illustrates a schematic lateral view of a further embodiment of the implant according to the invention.

The embodiment of a sack 500 illustrated in FIG. 6 which is substantially similar to the sack 1 except as noted below, extends longitudinally from a first end 520 to a second end 521 and includes a plurality of chambers 504 along a length thereof. In addition, the sack 500 similarly includes a first opening 502 at the first end 520. The sack 500, however, further includes a second opening 502' at the second end 521, which may also be configured as a second stop valve 524'. The second stop valve 524' is in fluid connection with the chamber 504 which is closest to the second end 521 of the sack 500. Since there may be two openings 502, 502', the chambers 504 of the sack 500 do not have to be filled with a filling material 512 during the manufacture of the sack 500 but may also be filled through the second valve 524' with the filling material 512. The non-return valves 505 may be integrated in the dividing walls 511 of the sack 500 such that flow is directed through each of the non-return valves 505 in the same direction so that each non-return valves 505 opens when the pressure in a chamber 504 into which a side of the valve 505 closer to the opening 502 opens is lower than a pressure in a chamber into which a side of the valve 505 further from the opening 502 opens. Thus, when the filling material 512 is inserted into the chamber 504 in fluid connection with the second opening 502', the adjacent chamber 504 will have a lower pressure than the chamber 504 into which the filling material 512 has been inserted so that the non-return valve 505 connecting the two chambers 504 opens allowing the filling material to pass therethrough into the adjacent chamber 504. The chambers 504 may be evacuated of a gas and/or fluid surrounding the filling material 512 in a similar manner via the stop valve 524 located at the first end 520 of the sack 500.

Figure 7:
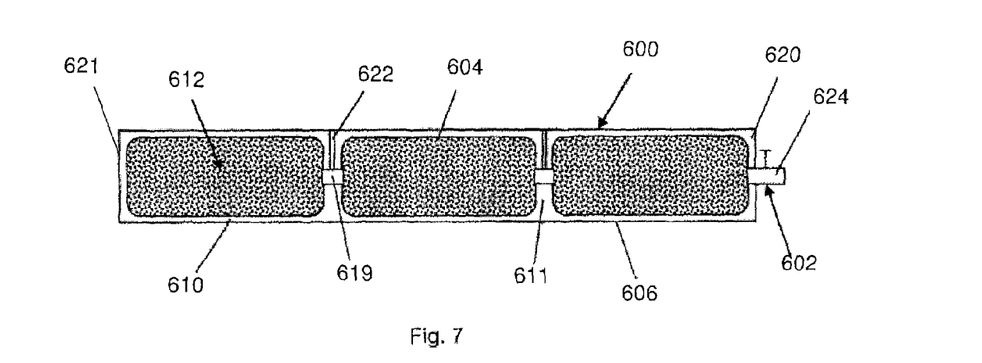
FIG. 7 illustrates a schematic lateral view of again a further embodiment of the implant according to the invention.

FIG. 7 illustrates an embodiment of a sack 600 substantially similar to the sack 1, as described above, comprising an envelope 610 extending longitudinally from a first end 620 to a second end 621 and including a plurality of chambers 604 positioned along a length thereof. The sack 600 differs from the sack 1 only in that adjacent chambers 604 are interconnected via directional control valves 619, which may be opened or closed by a control member 622. The control member 622 may, for example, extend through dividing walls 611, between the chambers 604 to an outer peripheral surface 606 of an envelope 610 of the sack 600 so that the directional control valves 622 may be operated from outside of the sack 600. It will be understood by those of skill in the art, however, that the control member 622 may be arranged in any of a variety of ways so long as the control member 622 is accessible from outside of the sack 600. In this embodiment, the sack 600 does not have to be filled with filling material 612 during manufacture of the sack 600. Rather, the chambers 604 may be filled with the filling material 612 through the opening 602 at the first end 620 of the sack 600 by opening the direction control valve 619 via the control member 622. Similarly to the sack 1, the opening 602 may be configured as a stop valve 624. The evacuation of the sack 600 may also be effected via the opening 602. The directional control valves 622 are opened such that the gas and/or fluid surrounding the filling material 612 passes between adjacent chambers 604 through the valve 619 and out of the opening 602 at the first end 620 of the sack 600. When the evacuation of the sack 600 is completed the directional control valves 622 are closed so that the individual chambers 604 are completely separated from one another.

Figure 8:
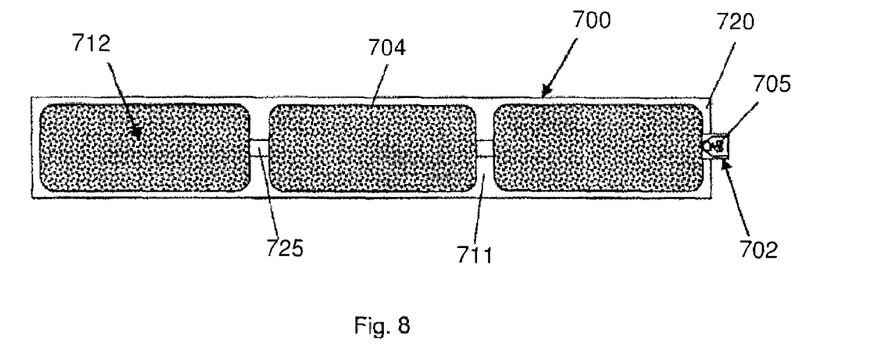
FIG. 8 illustrates a schematic lateral view of yet a further embodiment of the implant according to the invention.

FIG. 8 illustrates an embodiment of a sack 700 that may be substantially similar to the sack 1 comprising an envelope 710 extending longitudinally from a first end 720 to a second end 721 and including a plurality of chambers 704 therein along a length thereof. The sack 700 differs from the sack 1 only in that the adjacent chambers 704 are interconnected via a through opening 725 and that an opening 702 is configured as a non-return valve 705. The through openings 725 may extend through dividing walls 711 defining the chambers 704 so that the chambers 704 are in fluid communication with one another. Similarly to all of the embodiments of the invention, the openings 725 may be aligned long a longitudinal axis of the sack 700 or in any other configuration so that, when the implant is rigidized, it will assume a shape which will place the target portions of bone in the desired spatial relation to one another. The through openings 725 may remain open after evacuation of the chambers 704. In this case, the chambers 704 may not be obturated relative one another after the evacuation of the sack 700 has been completed. Alternatively, the through openings 725 may be obturated via welding or other sealing process. The chambers 704 may be filled with filling material 712 during manufacturing of the sack 700.

In an alternative embodiment, the opening 702 may be configured as a stop valve similar to the stop valve 24 of the sack 1, as shown in FIG. 1, or as a tubular collar similar to the tubular collar 123 of the sack 100, as shown in FIG. 2. In these embodiments, the opening 702 may be obturated by welding or tying off the tubular collar. Since adjacent chambers 704 are connected to one another by through openings 725, the chambers 704 may be filled with filling material 712 via the stop valve or tubular collar. After the chambers 704 have been evacuated, the opening 702 may obturated by, for example, welding closed the stop valve or tying off the tubular collar.

In a further alternative embodiment, the implant is substantially as described for the previous embodiments. In this further alternative embodiment, the sack is reinforced. The reinforcement is provided in a number of ways as would be understood by the skilled person. For example the reinforcement could be provided by one or a combination of reinforcement beams and fibers. Where the reinforcement includes beams, the beams are embedded in the wall of the sack and provide additional rigidity and stiffness to the implant. The reinforcement beams can be any suitable shape and configuration. For example, the reinforcement beams can be metal wires or rods that are arranged to run along the length of the sack either longitudinally or helically. Where the reinforcement includes fibers, the fibers may be arranged in a mesh or grid like configuration that is incorporated into the sack material. The fibers serve to reinforce the sack material and provide additional resistance to tearing of or fissure formation in the sack, especially during the evacuation process. The tearing or fissures could result from external influences, occur during insertion of the implant or could be due to filling material having sharp edges.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. An implant configured for implantation adjacent to or within target portions of bone to stabilize the target portions of bone in a desired spatial relation to one another, the implant comprising:
    a deformable gas tight sack comprising a first chamber in fluid communication with an obturatable opening, the sack including a second chamber in fluid communication with the first chamber via a connecting element opened and closed by a control member; and
    a filling material filling each of the first and second chambers and, in an initial configuration, a fluid surrounding the filling material so that, in the initial configuration, the implant is in a flexible insertion state;
    wherein, when the fluid surrounding the filling material is removed from the first and second chambers through the opening, a wall of the sack deforms around and presses against the filling material to hold the filling material, transitioning the implant from the insertion state to a relatively rigid fixation state in which the implant is fixable in the target portions of bone.

2. The implant according to claim 1, wherein each of the first and second chambers comprises a wall which, in the fixation state, deforms around and holds the filling material in the relatively rigid fixation state.

3. The implant according to claim 1, wherein the connecting element is one of a directional control valve, a non-return valve and a stop valve.

4. The implant according to claim 1, wherein the implant extends along a longitudinal axis from a first end to a second end and wherein the first and second chambers extend along the longitudinal axis.

5. The implant according to claim 1, wherein the sack comprises a stiff material.

6. The implant according to claim 1, wherein the opening includes a collar welded closed such that the sack is gas tight.

7. The implant according to claim 3, wherein the connecting elements are welded to close fluid communication between the first and second chambers.

8. The implant according to claim 1, wherein the sack includes a second valve at the second end thereof, the first and second chambers being fillable with the filling material via the second valve.

9. The implant according to claim 2, wherein the chambers are arranged both longitudinally and parallel relative to one another.

10. The implant according to claim 3, wherein at least one of the connecting elements includes a flexible tube.

11. The implant according to claim 1, wherein the filling material includes individual particles selected from the group comprising a sinterable thermoplastic, a thread, a fiber, a dye, a pigment and a chromophore.

12. The implant according to claim 1, wherein the sack and the filling material are resorbable.

13. The implant according to claim 1, wherein the first and second chambers include an inner chamber arranged concentrically within an outer chamber.

14. The implant according to claim 1, further comprising a passage extending transversely through the sack, the first and second chambers being gas tightly sealed with respect to the passage, the passage being sized and shaped to receive a fixation element therethrough.

15. The implant according to claim 1, wherein an outer wall of one of the first and second chambers of the sack defines a predetermined insertion shape.

16. A method for bone fixation comprising the steps of:
inserting an implant to a desired position within a bone cavity in a flexible insertion configuration, the implant including a gas tight sack including a first chamber therein and an obturatable opening at the first end in fluid communication with the first chamber, the sack including a first chamber and a second chamber in fluid communication with one another via a first connecting element opened or closed by a control member, the implant including a filling material and, in the insertion configuration, a fluid surrounding the filling material and filling the first chamber ; and
removing the fluid surrounding the filling material from the chambers to stiffen the implant into a fixation configuration in which the implant is substantially rigid and fixable into the bone cavity to maintain portions of the bone in a desired spatial relation to one another.

17. The method according to claim 16, further comprising the step of:
obturating the opening after removing filling material from the first chamber; and
sintering the filling material by supplying energy thereto.

18. The method according to claim 16, the sack including a third chamber in fluid communication with the second chamber via a second connecting element.

19. The method according to claim 18, further comprising the step of obturating the first and second connecting elements.

20. A kit for an implant, the kit comprising:
a deformable gas tight sack comprising a chamber in fluid communication with an obturatable opening, the sack including a first chamber and a second chamber in fluid communication with one another via a connecting element opened and closed by a control member; and
a filling material filling the first and second chambers, wherein, in a flexible initial state, a fluid surrounds the filling material, removal of the fluid from the first and second chambers deforming walls of the first and second chambers to press against the filling material therein and hold the filling material, transitioning the implant from the insertion state to a relatively rigid fixation state in which the implant is fixable in the target portions of bone.

* * * * *